United States Patent [19]

Shoesmith

[11] Plant 4,324

[45] Oct. 24, 1978

[54] CHRYSANTHEMUM NAMED SUN DEVIL

[75] Inventor: Leonard H. Shoesmith, Westfield-Woking, England

[73] Assignee: Pan-American Plant Company, West Chicago, Ill.

[21] Appl. No.: 878,939

[22] Filed: Feb. 17, 1978

[51] Int. Cl.[2] ..... A01H 5/00

[52] U.S. Cl. ..... Plt./78

[58] Field of Search ..... Plt./75, 78

*Primary Examiner*—Robert E. Bagwill

*Attorney, Agent, or Firm*—Chas. W. Rummler

[57] ABSTRACT

A new variety of chrysanthemum plant suitable for both greenhouse potted plant culture and as an outdoor garden chrysanthemum, characterized in particular by the clear yellow color of the ray florets of the medium sized, decorative flower form of its blooms which exhibit no bronzing when flowered under cool temperatures.

2 Drawing Figures

BACKGROUND OF THE NEW PLANT

This new variety of chrysanthemum originated as a seedling of unknown parentage grown at my breeding facilities at Westfield-Woking, Surrey, England, the new plant having been discovered by me among a field of seedlings of random pollinated plants cultivated by me with the object of finding new plants suitable for the commercial market. This new plant was selected by me for propagation and test because of its apparent ability to withstand cool flowering temperatures without bronzing and its attractive clear yellow color and form. Asexual propagation of this plant was done by me at Westfield-Woking, Surrey, England, by means of cuttings from the original plant and subsequent propagation, by vegetative cuttings, through successive generations has shown the novel characteristics of this new variety to hold true from generation to generation and to be firmly fixed.

DESCRIPTION OF THE DRAWINGS

This new chrysanthemum cultivar is illustrated by the accompanying drawings in which sheet one is a full color photograph rendition made in June 1977 of a potted plant of this variety in full bloom, the colors shown being as nearly true as it is reasonably possible to obtain by means of conventional professional photographic procedures; and sheet two is a mechanical print showing typical leaves of the plant taken at various stages of maturity.

DESCRIPTION OF THE NEW PLANT

The following is a detailed description of my new variety of chrysanthemum plant with the color descriptions according to the R.H.S. Colour Chart published by The Royal Horticultural Society of London, England.

THE PLANT

Origin: Seedling.

Parentage: Unknown, this seedling having been selected from a field resulting from random pollination of the parent plant.

Classification:

*Botanic.*—*Chrysanthemum morifolium*

*Commercial.*—Greenhouse pot plant and outdoor garden chrysanthemum.

Form: Perennial herbaceous bush.

Height: 18 to about 45 cm.

Growth: Upright and vigorous, sturdy with average strength.

Branching: Average under natural conditions.

Foliage: Sparse in quantity with 7 to 9 leaves per 10 cm. of stem length.

*Size of leaf.*—About 5.5 to 10.4 cm. in length and about 3.6 to 6.4 cm. in width. Shape: Lobed, lanceolate with dentate margins. Surface aspect: Canescent. Color: Upper side — RHS 147A. Under side — RHS 147B. Venation: Pinnate. Petioles: About 1.5 to 2.8 cm.

THE BUD

Form: Elliptical.

Size: About 5 to 7 mm. in diameter; about 3 to 4 mm. in depth.

Opening: Slowly.

Color:

*When the phyllaries first divide.*—RHS 144A.

*When florets begin to unfurl.*—9A, 13A, 13B.

Phyllaries: The receptacle, on its outside, bears many involucral bracts which are spear-shaped and upstanding.

*Color.*—Inside — RHS 137A. Outside — RHS 137A.

*Surface texture.*—Pubescent.

Peduncle: Erect and about 2.2 to 3.7 cm. in length.

*Surface texture.*—Pubescent.

THE FLOWER

Flowering characteristics: This variety can be flowered the year around with photoperiod control.

*Response.*—7-week.

*Recommended flowering.*—March 1 to November 1.

*Natural season flowering.*—September 15 to September 24.

Blooms: Flower type — Composite and decorative.

*Borne.*—A head of many florets borne on a receptacle.

*Size.*—Small. About 3.9 to 5.3 cm. in diameter and about 1.9 to 2.6 cm. in depth.

*Shape.*—Cup-shaped when bloom first opens becoming hemispherical as bloom matures.

*Florets.*—Numerous in quantity. Form: Decorative. *Color.*—

| | August | September | October | November |
|---|---|---|---|---|
| Outer Floret | | | | |
| Upper Side - | 5A | 5B | 6A | 6B |
| Under Side - | 5B | 5C | 7D | 8B |
| Inside Floret | | | | |
| Upper Side - | 9A | 9A | 7A | 9B |
| Under Side - | 9A | 9B | 8A | 10A |

Tonality at 2 meters: 9A

Firmness: Medium. Appearance: Very slight shine. Discoloration: Very slight fade.

Peduncle: Upright and sturdy. Length: About 2.2 to 3.7 cm. Color: 146A.

Persistence: Florets hang on and dry.

Fragrance: Typical chrysanthemum.

Lasting quality: 3 to 5 weeks on the plant. Not recommended as a cut flower.

REPRODUCTIVE ORGANS

Stamens: 5-syngenesious anthers.

*Filaments.*—About 1 to 3 mm. long. Color: Light yellow.

*Pollen.*—Color — Yellow.

Pistils: Number — One to each ray and disc floret.

*Styles.*—About 3 to 5 mm. long.

*Stigmas.*—Color — Yellow.

Ovaries: Inferior bicarpellate.

This new variety of chrysanthemum is particularly characterized by its medium-sized blooms of decorative flower form which exhibit a clear yellow color in its ray florets, by the fact that the clear yellow color does not bronze when the plant is flowered under cool temperatures, and by its 7-week flowering response. This new plant also has a relatively upright plant habit with medium plant height, strong stems and small to medium-sized foliage.

I claim:

1. A new variety of chrysanthemum plant, substantially as herein shown and described, characterized by the clear yellow color of the ray florets of its medium-sized blooms of decorative flower form, by its 7-week flowering response, by its relatively upright plant habit, and by its medium plant height with strong stems and small to medium-sized foliage.

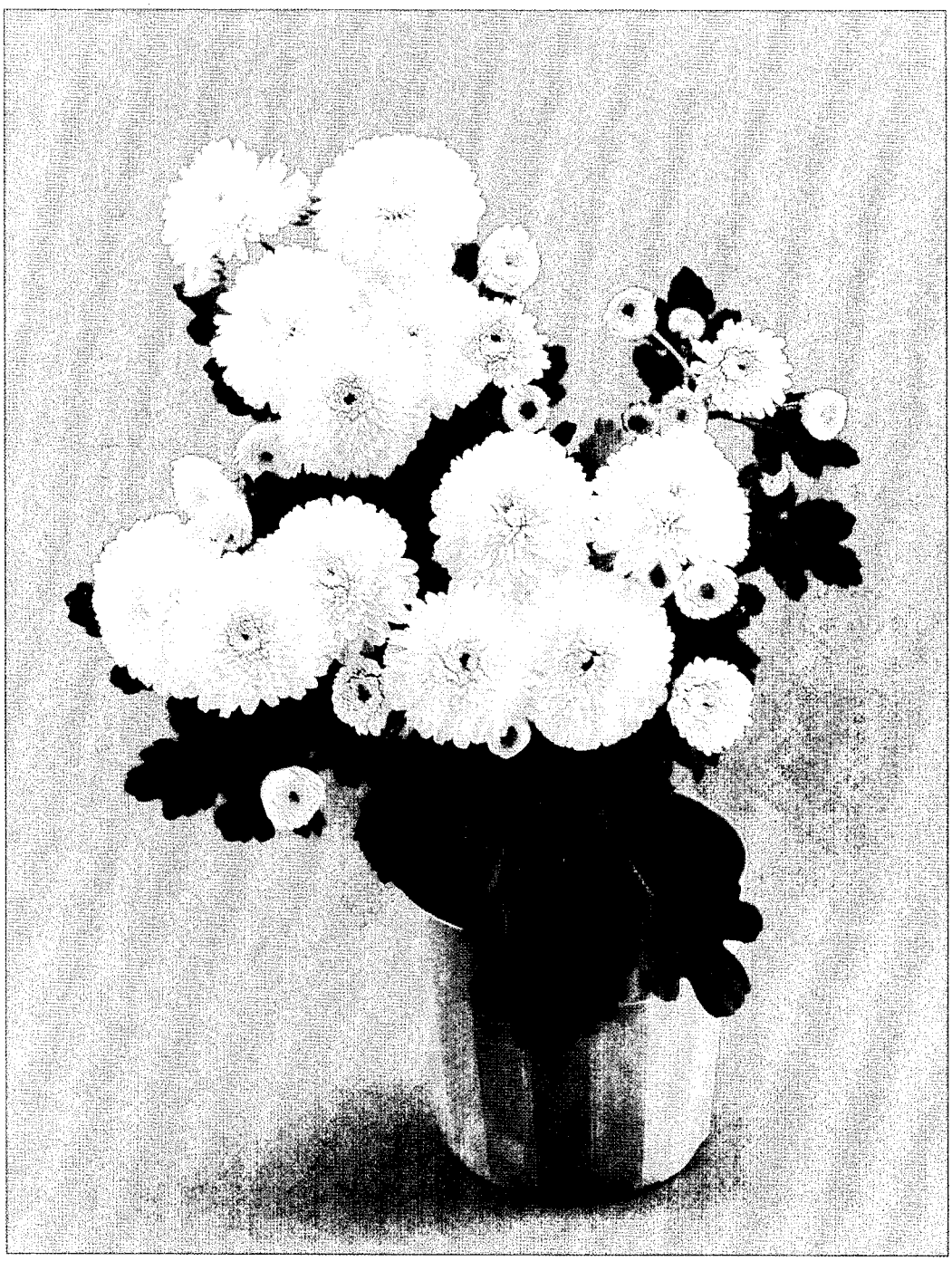

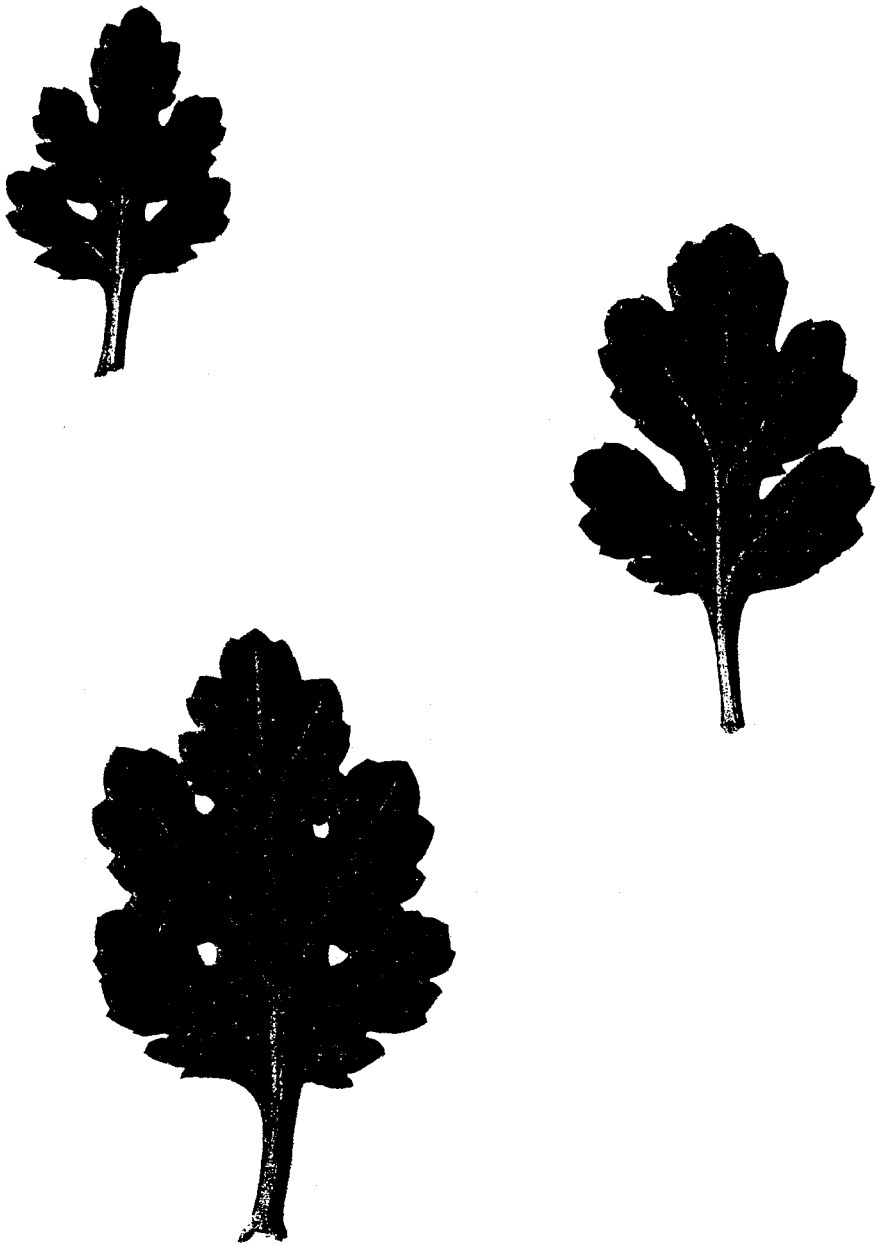

* * * * *